United States Patent
Wada et al.

(10) Patent No.: US 10,632,089 B2
(45) Date of Patent: Apr. 28, 2020

(54) TYROSINASE ACTIVITY INHIBITOR AND EXTERNAL PREPARATION FOR SKIN

(71) Applicant: JO Cosmetics Co., Ltd., Ota-ku, Tokyo (JP)

(72) Inventors: Kanako Wada, Tokyo (JP); Katsura Adachi, Tokyo (JP)

(73) Assignee: JO Cosmetics Co., Ltd., Ota-ku, Tokyo (JP)

( * ) Notice: Subject to any disclaimer, the term of this patent is extended or adjusted under 35 U.S.C. 154(b) by 0 days.

(21) Appl. No.: 15/565,746

(22) PCT Filed: Apr. 7, 2016

(86) PCT No.: PCT/JP2016/061343
§ 371 (c)(1),
(2) Date: Oct. 11, 2017

(87) PCT Pub. No.: WO2016/170990
PCT Pub. Date: Oct. 27, 2016

(65) Prior Publication Data
US 2018/0071239 A1 Mar. 15, 2018

(30) Foreign Application Priority Data
Apr. 18, 2015 (JP) ................................. 2015-085493
Apr. 18, 2015 (JP) ................................. 2015-085494

(51) Int. Cl.
| | | |
|---|---|---|
| A61K 31/198 | (2006.01) | |
| A61K 8/44 | (2006.01) | |
| A61Q 19/02 | (2006.01) | |
| A61K 31/4172 | (2006.01) | |
| A61K 31/4415 | (2006.01) | |
| A61K 8/49 | (2006.01) | |
| A61K 31/385 | (2006.01) | |
| A61K 31/665 | (2006.01) | |
| A61K 45/06 | (2006.01) | |
| A61K 8/66 | (2006.01) | |
| A61K 8/67 | (2006.01) | |
| A61K 31/315 | (2006.01) | |
| A61K 31/375 | (2006.01) | |
| A61K 38/44 | (2006.01) | |

(52) U.S. Cl.
CPC .............. *A61K 31/198* (2013.01); *A61K 8/44* (2013.01); *A61K 8/447* (2013.01); *A61K 8/49* (2013.01); *A61K 8/4946* (2013.01); *A61K 8/4986* (2013.01); *A61K 8/66* (2013.01); *A61K 8/676* (2013.01); *A61K 31/315* (2013.01); *A61K 31/375* (2013.01); *A61K 31/385* (2013.01); *A61K 31/4172* (2013.01); *A61K 31/4415* (2013.01); *A61K 31/665* (2013.01); *A61K 38/446* (2013.01); *A61K 45/06* (2013.01); *A61Q 19/02* (2013.01); *Y02A 50/473* (2018.01)

(58) Field of Classification Search
None
See application file for complete search history.

(56) References Cited

U.S. PATENT DOCUMENTS

| | | | | |
|---|---|---|---|---|
| 2004/0092586 A1* | 5/2004 | Ogata | .................. | A61K 31/185 514/494 |
| 2004/0131563 A1* | 7/2004 | Mundt | .................. | A61K 8/4966 424/59 |
| 2009/0093541 A1* | 4/2009 | Ogata | ...................... | A61K 8/46 514/494 |
| 2012/0213719 A1* | 8/2012 | Kang | ..................... | A61Q 19/02 424/62 |

FOREIGN PATENT DOCUMENTS

| | | |
|---|---|---|
| JP | 64-27470 A | 1/1989 |
| JP | 06-135832 A | 5/1994 |
| JP | 06-507165 A | 8/1994 |
| JP | 06-245763 A | 9/1994 |
| JP | 10-007541 A | 1/1998 |
| JP | 2003-286168 A | 10/2003 |
| JP | 2006-124356 A | 5/2006 |
| JP | 2006-206561 A | 8/2006 |
| WO | 02/076935 A1 | 10/2002 |
| WO | 2004/024139 A1 | 3/2004 |

OTHER PUBLICATIONS

International Search Report of PCT/JP2016/061343 dated Jul. 12, 2016 [PCT/ISA/210].

* cited by examiner

*Primary Examiner* — Jared Barsky
(74) *Attorney, Agent, or Firm* — Sughrue Mion, PLLC

(57) ABSTRACT

A tyrosinase activity inhibitor is prepared by combining (A) a metal (zinc, cobalt or iron) chelate compound of α-lipoyl amino acid or its pharmaceutically acceptable salt with (B-1) a human manganese SOD or (B-2) an ascorbic acid compound such as ascorbic acid and ascorbyl glucoside. A ratio (R1) of the (B-1) component content to the (A) component content is preferably 0.001 to 1,500, when R1 is defined as R1=[Unit concentration of (B-1) component (unit/mL)/Concentration of (A) component (μg/mL)], and a ratio (R2) of the (A) component content to the (B-2) component content is preferably 0.0001 to 1,000, when R2 is defined as R2= [Concentration of (A) component (m/mL)/Concentration of (B-1) component (mg/mL)]. An external preparation for skin contains the (A) component and the (B-1) component or the (B-2) component as effective ingredients for inhibiting tyrosinase activity.

7 Claims, No Drawings

TYROSINASE ACTIVITY INHIBITOR AND EXTERNAL PREPARATION FOR SKIN

CROSS REFERENCE TO RELATED APPLICATIONS

This application is a National Stage of International Application No. PCT/JP2016/061343, filed Apr. 7, 2016, claiming priorities based on Japanese Patent Application Nos. 2015-085493 and 2015-085494 filed Apr. 18, 2015, the contents of all of which are incorporated herein by reference in their entirety.

DETAILED DESCRIPTION OF THE INVENTION

Technological Field

The present invention relates to a novel tyrosinase inhibitor and an external preparation for skin containing the same.

Background Technology

Alpha-lipoic acid (another name: thioctic acid or 6,8-dithiooctanoic acid) is an important coenzyme existing abundantly in mitochondria and draws attention as a curative for various pathological conditions induced by oxidative stress because of its antioxidative ability. A reduced dimercaptooctanoic acid has a function to regenerate reductively oxidized glutathione or vitamin C. Focusing on such an anti-oxidative ability of α-lipoic acid, investigations have been conducted to utilize α-lipoic acid as a raw material for pharmaceuticals and cosmetics. For example, Patent Document 1 discloses that metal chelate compounds of α-lipoyl amino acid, i.e., acid amide formed by reacting α-lipoic acid with amino acid, or pharmaceutically acceptable salts thereof function to inhibit activity of tyrosinase that is known as an enzyme involved in production of melanin and activity of elastase that is a degrading enzyme of elastin existing in skin tissue, and are useful as a preventive agent or curative for stain, freckle and sunburn on skin, a skin-whitening agent, a skin-beautifying agent, an anti-wrinkle agent and the like.

Patent Document 2 discloses that a non-chelated α-lipoyl amino acid or its pharmaceutically acceptable salt exhibits elastase inhibitory activity as well as an effect for inhibiting production of melanin. The document also discloses an external preparation for skin containing the compound as an effective component that is suitable for a preventive agent or curative for stain, freckle and sunburn on skin, a skin-whitening agent and a skin-beautifying agent. Hereinafter, the α-lipoyl amino acid and its pharmaceutically acceptable salt described in Patent Documents 1 and 2 are sometimes collectively referred to as "α-lipoic acid derivatives". Further, Patent Document 3 discloses that a metal chelate compound of α-lipoyl amino acid exhibits an effect for reducing deposition caused by agglomeration of melanin pigment such as stain, freckle and lentigines on skin. Of these, the α-lipoic acid derivatives described in Patent Document 1 exhibit an excellent tyrosinase inhibitory activity in particular. In recent years, however, there has been a demand to develop a material exhibiting more excellent tyrosinase inhibitory activity in the field of cosmetics.

Meanwhile, superoxide dismutase is known as a primary enzyme having an antioxidative ability for treating an active oxygen that causes oxidative stress in a human body. Hereinafter, superoxide dismutase is sometimes referred to as "SOD". There are known three kinds of SODs, i.e., SOD1, SOD2 and SOD3 concerning mammals including human beings. Both SOD1 and SOD3 have copper and zinc in each active center. SOD1 is a dimer composed of two units and exists in a cytoplasm while SOD3 is a tetramer composed of four units and exists in a space outside cell. Further, SOD2 has manganese in its active center and is a tetramer composed of four units having a molecular weight of 24.8 kDa, and localizes in a mitochondria. This manganese SOD functions to assist a reaction for making oxygen and hydrogen peroxide from superoxide anion in the mitochondria. The hydrogen peroxide generated is decomposed to water and oxygen by an action of catalase or other enzymes.

Conventionally, there has been conducted an investigation to use SOD, its analog or variant as a component of medicines or cosmetics. Patent Document 4 describes that human manganese SOD, its analog or its mutant is useful as a therapeutic agent for synovial inflammation, arthritis or pulmonary fibrosis. In Patent Document 4, the term "human manganese SOD analog" means human manganese SOD in which one or more additional amino acids are bound at one or both ends, and the term "human manganese SOD mutant" means substantially equivalent to the human manganese SOD regardless of having an amino acid sequence containing one or more different amino acids from that of human manganese SOD.

In addition, Patent Document 5 describes a cosmetic for skin or hair which contains SOD and a phosphonic acid derivative in combination. This document describes that the cosmetic has a function of maintaining keratin structures of skin or hair, and can protect skin from harmful effects of ultraviolet rays. Also, this patent document describes that, among several types of SODs, those having copper and zinc as active centers, that is, SOD 1 or SOD 3 are preferable.

Furthermore, Patent Document 6 discloses that, in the peptide sequence of human manganese SOD, amino acid residues present at sites where replacement of amino acid residues with other amino acid residues does not affect an enzyme activity are replaced with more positively charged amino acid residues to obtain human manganese mutant SOD having an isoelectric point raised by the substitution. Patent Document 6 also discloses that significant raise of the isoelectric point enables the human manganese mutant SOD to readily permeate into skin tissue, whereby the human manganese mutant SOD exhibits pharmacological effects on various inflammatory diseases, cancer, hypertension and the like, and it is useful as an ingredient of cosmetics (see paragraph 0075). Although Patent Document 6 discloses that the human manganese mutant SOD can be used for preparing a cosmetic, however, there is no specific description concerning a cosmetic containing the human manganese mutant SOD, as well as properties exhibited when it is used as an ingredient of a cosmetic.

Although ascorbic acid is completely different in a chemical structure from α-lipoic acid derivatives and SOD, it is also widely known as an antioxidant. Ascorbic acid has optical isomers, and the L form is known as vitamin C, and it participates in various oxidation-reduction reactions in vivo. In the field of cosmetics, ascorbic acid, its derivative or its salt is added in many products. In particular, there are many proposals on its addition in a skin-whitening cosmetic for the purpose of improving dark skin, spots, buckwheat or the like.

Attempts to use α-lipoic acid in combination with ascorbic acid have also been known for a long time. For example, Patent Document 7 discloses a medicine containing a lipoic acid compound such as α-lipoic acid and dihydrolipoic acid, and vitamins such as vitamin A, vitamin B1, vitamin B6, vitamin B12, vitamin E and vitamin C (see claim 2). Then, the patent document discloses that ampoules and tablets containing equal amounts of α-lipoic acid and vitamin C (L-ascorbic acid) were prepared (see Examples 3 and 4). However, this patent document is silent about a cosmetic containing α-lipoic acid and vitamin C in combination.

Patent Document 8 discloses an external preparation for skin containing a lipoic acid compound and a compound selected from vitamin A, carotenoids, vitamin B6, vitamin C and so on. This patent document also discloses that the combination synergistically improves an effect of erasing active oxygen species, and whereby rough skin and skin aging symptom can be improved, and skin-whitening effect can be obtained (see paragraph 0006). The examples of the patent document show that rough skin symptoms and pigmentation are improved in both the composition containing lipoic acid and ascorbic acid (Example 1) and the composition containing dihydrolipoic acid and retinol palmitate, i.e., vitamin A derivative (Example 4) (see Table 7). However, as is apparent from the data of Comparative Examples described later, the external preparation for skin described in the patent document is not necessarily sufficient in an ability of inhibiting tyrosinase activity, and further improvement has been desired.

PRIOR ART DOCUMENT

Patent Document

Patent Document 1: PCT International Publication 2002/076935
Patent Document 2: Japanese Unexamined Patent Application Publication No. 2003-286168
Patent Document 3: PCT International Publication 2004/024139
Patent Document 4: Japanese Unexamined Patent Application Publication No. H01-27470
Patent Document 5: Re-publication of PCT International Publication No. JPH06-507165
Patent Document 6: Japanese Unexamined Patent Application Publication No. H06-245763
Patent Document 7: Japanese Unexamined Patent Application Publication No. H06-135832
Patent Document 8: Japanese Unexamined Patent Application Publication No. H10-007541

DISCLOSURE OF THE INVENTION

Problems to be Solved by the Invention

As a result of intensive research under the background art, the present inventors have found that when a specific α-lipoic acid derivative is used in combination with a specific human SOD or a specific ascorbic acid compound, an excellent ability to inhibit tyrosinase activity is obtained as compared with the case where each compound is used solely. The present invention was completed based on such a knowledge.

A main object of the present invention is to provide a tyrosinase activity inhibitor having highly excellent ability to inhibit tyrosinase activity. Another object is to provide an external preparation for skin which is capable of inhibiting an activity of tyrosinase contained in skin, and is useful as a skin-whitening agent and the like.

Means Used to Solve the Problem

The objects of the present invention are achieved by making a tyrosinase activity inhibitor that contains a specific metal chelate compound of α-lipoyl amino acid or a pharmaceutically acceptable salt thereof and a specific human SOD or a specific ascorbic acid compound in combination.

Thus, the present invention provides, as a first embodiment, a tyrosinase activity inhibitor that is a combination of (A) a metal chelate compound of α-lipoyl amino acid represented by the following formula (1) or a pharmaceutically acceptable salt thereof, and (B-1) human manganese SOD or (B-2) at least one of ascorbic acid compounds selected from the group consisting of ascorbic acid, ascorbyl glucoside, ascorbic acid phosphoric acid monoester and salts thereof. In another aspect, the present invention also provides an external preparation for skin comprising (A) a metal chelate compound of α-lipoyl amino acid represented by the following formula (1) or a pharmaceutically acceptable salt thereof, and (B-1) human manganese SOD or (B-2) at least one of ascorbic acid compounds selected from the group consisting of ascorbyl glucoside, ascorbic acid phosphoric acid monoester and salts thereof.

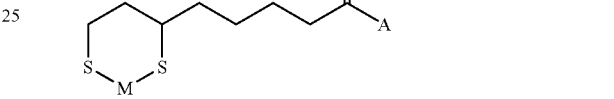

(1)

In the formula (1), M represents a metal selected from zinc, cobalt and iron, and A represents an N-linked amino acid residue.

Effects of the Invention

According to the present invention, use of a specific α-lipoic acid derivative in combination with a specific human SOD or a specific ascorbic acid compound makes it possible to obtain a tyrosinase activity inhibitor that is excellent in an ability to inhibit tyrosinase activity. Also, a formulation containing a specific α-lipoic acid derivative and a specific human SOD or a specific ascorbic acid compound as an effective component makes it possible to obtain an external preparation for skin that can effectively inhibit an activity of tyrosinase and is excellent in skin-whitening property.

EMBODIMENTS FOR CARRYING OUT THE INVENTION

Hereinafter, the present invention will be described in detail.
<Tyrosinase Activity Inhibitor>
The tyrosinase activity inhibitor of the present invention is a combination of (A) a metal chelate compound of an acid amide formed by α-lipoic acid and an amino acid, or its pharmaceutically acceptable salt, and (B-1) a human manganese superoxide dismutase or (B-2) a specific ascorbic acid compound. In the following description, the metal chelate compound of an acid amide formed from α-lipoic acid and an amino acid or its pharmaceutically acceptable salt thereof, the human manganese superoxide dismutase and the specific ascorbic acid compound are sometimes abbreviated as "(A) component", "(B-1) component" and "(B-2) component", respectively. In addition, (B-1) component and (B-2) component may be collectively referred to as "(B) component". The above-mentioned (A) component and (B) component may be mixed in advance to make a composition. Also, each component may be separately stored and independently added when preparing a desired product such as an external preparation for skin.

<α-Lipoic Acid Derivative>

The tyrosinase activity inhibitor of the present invention uses a metal chelate compound of α-lipoyl amino acid or its pharmaceutically acceptable salt as an active ingredient. The metal chelate compound of α-lipoyl amino acid is a compound where α-lipoic acid is combined with an amino acid via an amide bond, and subsequently combined with a metal via chelate bond, and is represented by the above formula (1).

In the present invention, the term "amino acid" refers to amino acids having a carboxyl group and an amino group in the same molecule, for example, aliphatic amino acids such as so-called α-amino acid, β-amino acid, γ-amino acid, δ-amino acid, ε-amino acid and the like; alicyclic or aromatic amino acids such as aminomethylcyclohexane carboxylic acid, anthranilic acid and the like; and aminoalkanesulfonic acids having a sulfonic acid group and an amino group in the same molecule. Examples of α-amino acid include glycine, alanine, valine, leucine, isoleucine, serine, threonine, tyrosine, cysteine, methionine, aspartic acid, asparagine, glutamic acid, glutamine, arginine, lysine, histidine, phenylalanine, tryptophan and the like. Examples of β-amino acid include β-alanine, examples of γ-amino acid include γ-amino-n-butyric acid (GABA) and carnitine, examples of δ-amino acid include 5-aminolevulinic acid and 5-aminovaleric acid, and examples of ε-amino acid include δ-aminohexanoic acid and the like. Examples of aminoalkanesulfonic acid include aminoethanesulfonic acid (taurine) and the like. Of these amino acids, methionine, histidine, phenylalanine, γ-amino-n-butyric acid, δ-aminohexanoic acid, anthranilic acid and aminoethanesulfonic acid are preferred.

As a metal for making a metal chelate compound of α-lipoyl amino acid, zinc, cobalt or iron can be used. Of these, when zinc is used, a stable chelate compound can be obtained.

Pharmaceutically acceptable salts of the chelate compound include alkali metal salts such as sodium salt and potassium salt, and alkaline earth metal salts such as calcium salt and magnesium salt. Even salts other than these salts may be appropriately used as long as they are pharmaceutically acceptable.

Preferred specific examples of such a metal chelate compound of α-lipoyl amino acid or its pharmaceutically acceptable salt include zinc chelate compound of N-(6,8-dimercaptooctanoyl)-L-histidine sodium salt (hereinafter sometimes referred to as histidine dithiooctanamide (Na/zinc), zinc chelate compound of sodium N-(6,8-dimercaptooctanoyl) aminoethanesulfonate, zinc chelate compound of potassium N-(6,8-dimercaptooctanoyl) aminoethanesulfonate, zinc chelate compound of N-(6,8-dimercaptooctanoyl) glycine sodium salt, zinc chelate compound of sodium N-(6,8-dimercaptooctanoyl) aspartate, zinc chelate compound of sodium N-(6,8-dimercaptooctanoyl)-δ-aminohexanoate, zinc chelate compound of sodium N-(6,8-dimercaptooctanoyl)-γ-amino-n-butyrate, zinc chelate compound of N-(6, 8-dimercaptooctanoyl) phenylalanine sodium salt, chelate compound of sodium N-(6,8-dimercaptooctanoyl) alanthranilate, zinc chelate compound of N-(6,8-dimercaptooctanoyl) methionine, zinc chelate compound of N-(6,8-dimercaptooctanoyl) cysteine and the like. Also, cobalt chelate compounds and iron chelate compounds corresponding to these compounds are exemplified These compounds can be used in the form of monohydrate, dihydrate, ½ hydrate, ⅓ hydrate, ¼ hydrate, ⅔ hydrate, 3/2 hydrate or 6/5 hydrate.

Of these, histidine dithiooctanamide (Na/zinc) has been used as a cosmetic raw material, and is preferably used as a compound that is confirmed to be safe. It is possible to use commercially available products such as "DM-His. Zn" manufactured by Oga Research Co., Ltd. as the histidine dithiooctanamide (Na/zinc).

The metal chelate compound of α-lipoyl amino acid or its pharmaceutically acceptable salt can be obtained by synthesizing α-lipoyl amino acid as an intermediate and reducing it with a metal and an acid.

Usually, α-lipoyl amino acid is produced by protecting a carboxylic acid moiety which is an acidic group of an amino acid via its esterification, then converting to protected α-lipoic acid amide using α-lipoic acid and a dehydrating condensation agent, and finally saponifying protected α-lipoic acid amide. More specifically, at first α-lipoic acid is dissolved in an organic solvent such as chloroform, tetrahydrofuran and acetonitrile, and then to the resultant solution, a halogenated carbonate ester such as ethyl chlorocarbonate and butyl chlorocarbonate and a mixed acid anhydride reagent such as isobutyloxycarbonyl chloride, diethylacetyl chloride and trimethylacetyl chloride are added in the presence of tertiary amine such as triethylamine, tributylamine and N-methylmorpholin at a temperature of −15° C. to −5° C. to produce a mixed acid anhydride of α-lipoic acid. The reaction time is from about 1 to 2 minutes to several tens of minutes.

Next, an amino acid dissolved in a solvent such as alcohol, water or a mixture thereof is added to a reaction mixture in the presence of a base such as sodium hydroxide, potassium hydroxide, and a tertiary amine, e.g., trimethylamine and tributylamine to make reaction with the mixed acid anhydride of α-lipoic acid. After completion of the reaction, α-lipoyl amino acid can be obtained in a high yield by carrying out recrystallization using an appropriate solvent such as water or alcohol.

Subsequently, the α-lipoyl amino acid is reduced with zinc, cobalt or iron and an acid to obtain a metal chelate compound via a dihydro-α-lipoyl amino acid. Examples of the acid used for the reduction reaction of α-lipoyl amino acid include inorganic acids such as hydrochloric acid and sulfuric acid, and organic acids such as acetic acid and citric acid. Examples of the metal used for the reduction reaction include zinc powder, cobalt powder, iron powder and the like. In the case of a zinc chelate compound, it is considered that two SH groups (mercapto groups) in a molecule are chelated by bonding with one metallic atom.

The above synthesis method can be represented by the following reaction formula (I). In the formula, A and M have the same meanings as in the formula (1).

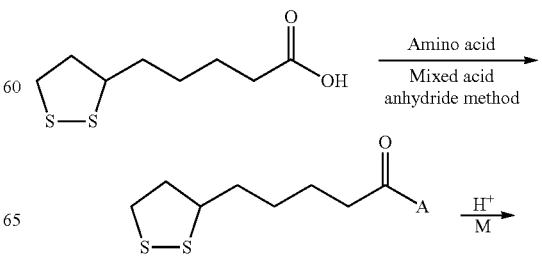

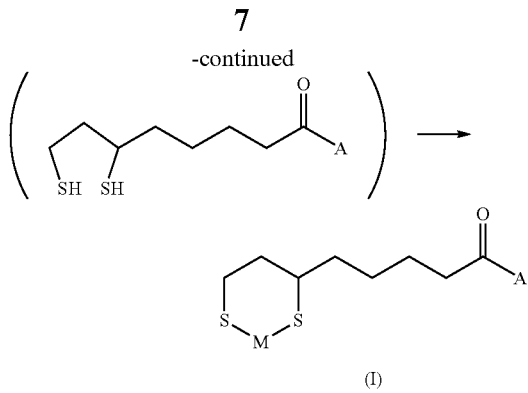

(I)

In the tyrosinase activity inhibitor of the present invention, the (B-1) human manganese SOD or the (B-2) specific ascorbic acid compound is used in combination with the (A) component. Components (B-1) and (B-2) will be described in order below.

<Human Manganese SOD>

Conventionally, the existence of SOD 1, SOD 2 and SOD 3 has been known as a human SOD as described above. In the present invention, it is essential to use human manganese SOD, which is known as SOD 2, among these human SODs. Even if SOD 1 and SOD 3 having copper and zinc in an active center are used, the objects of the present invention cannot be achieved.

Barra, D., et al. report that human manganese SOD is a tetramer of a peptide having a molecular weight of about 20,000 containing manganese in an active center, and the number of amino acids constituting one unit is 196, and they disclose its amino acid sequence (Barra, D. et al., J. Biol. Chem., 259, 12595-12601, 1984). On the basis of this knowledge, technology for synthesizing human manganese SOD by genetic recombination technology using Escherichia coli or yeast has been developed, and specific production methods are proposed in JP-A-H01-63383 and JP-A-H04-117288. As a result, in addition to human manganese SOD extracted from organs of animals including human being, human manganese SOD can be obtained by a genetic engineering production method at present. For example, SOD obtained by recombinant synthesis using yeast is commercially available as "Yeast Extract (SOD)" (enzyme unit concentration 3,000 units/mL) from Biox Technologies. As to the enzyme unit (SOD) unit, it is defined by J. McCord and Fridovittch in J. Biol. Chem. 244, 6049 (1969).

In the present invention, it is also possible to use analogues or mutants in which a part of the amino acid sequence of human manganese SOD is modified. Specific examples of the human mutant manganese SOD include, for example, MHS:Mn-SOD described in Examples 1-1 to 4 of Patent Document 6, and MHS 2:Mn-SOD described in Examples 11 to 16 of the same document. Incidentally, MHS:Mn-SOD has a peptide sequence in which a serine group being the third amino acid from the N-terminus in the human mutant manganese SOD is substituted with an arginine group, and has an isoelectric point of about 8.2. Further, MHS 2:Mn-SOD has a peptide sequence in which a serine group being the third amino acid from the N-terminus in the human mutant manganese SOD is substituted with an arginine group, a glutamine group being the 42nd amino acid from the N-terminus is substituted with a valine group, and has an isoelectric point of about 8.5 to 9.4 (see paragraphs 0060, 0061 and 0072 of Patent Document 6).

In the peptide sequence of human manganese SOD, the sequence of amino acids necessary for maintaining the enzyme activity (conserved amino acids) is described in Patent Document 6. With reference to the sequence, amino acids other than the conserved amino acids may be appropriately substituted with amino acids capable of increasing an isoelectric point while maintaining the conserved amino acids. For example, substitution of a serine residue with a basic amino acid residue such as arginine, lysine and histidine, or substitution of a glutamic acid residue with a neutral amino acid residue such as valine, leucine, isoleucine, glycine and alanine or a basic amino acid residue such as arginine, lysine and histidine enables the isoelectric point to be increased.

Human manganese SOD is often obtained in the form of an aqueous solution, but its form is not limited thereto. For example, it may be powdery in which it is encapsulated in cyclodextrin or the like for the purpose of stabilization.

In the present invention, it is important to combine the (A) component and the (B-1) component to make a tyrosinase activity inhibitor. When a ratio of both components (R1) is defined as the following equation, R1 is usually in the range of 0.001 to 1,500, preferably 0.1 to 500, more preferably 0.2 to 200.

$R1$=[Unit concentration of ($B$) component (Unit/mL)/ Concentration of ($A$) component (μg/mL)].

If the ratio of the (B-1) component is excessively low, the ability to inhibit tyrosinase activity cannot be enhanced. To the contrary, if the ratio is excessively high, the ability to inhibit tyrosinase activity does not increase as compared with the case using the (A) component alone, and it becomes economically disadvantageous.

The number of units of the (B-1) component can be measured as follows based on the description of Joe M. McCord, et al., J. Biol. Chem., 244, 6049-6055 (1969). First, 3 mL of a test solution containing $10^{-4}$ M EDTA and adjusted to pH 7.8 with 0.05 M potassium phosphate buffer is placed in a cuvette of 1 cm and maintained at 25° C. This test solution contains $1\times10^{-5}$ M ferricytochrome c, $5\times10^{-5}$ M xanthine and an appropriate amount of xanthine oxidase to reduce an absorbance at 550 nm of ferricytochrome c at a rate of 0.025 per minute. Under this condition, the amount of SOD that reduces the rate of decrease of cytochrome c to 50% is defined as the activity of 1 unit.

<Ascorbic Acid Compounds>

In the present invention, the ascorbic acid compounds used as the (B-2) component are at least one compound selected from ascorbic acid, ascorbyl glucoside, ascorbic acid phosphoric acid monoester and salts thereof. Incidentally, ascorbyl glucoside refers to 2-O-α-D-glucopyranosyl-L-ascorbic acid, and ascorbic acid phosphoric acid monoester refers to an ester having an ester bond between a hydroxyl group at 2- or 3-position of ascorbic acid and phosphoric acid. Among the ascorbic acid phosphoric acid monoesters, ascorbic acid-2-phosphate ester in which the hydroxyl group at 2-position is bonded to phosphoric acid via an ester bond is preferable.

Examples of salts of the ascorbic acid, the ascorbyl glucoside or the ascorbic acid phosphoric acid monoester include alkali metal salts such as sodium salt and potassium salt; alkaline earth metal salts such as magnesium salt, calcium salt and barium salt; ammonium salt; and amine salts such as monoethanolamine salt, diethanolamine salt, triethanolamine salt, monoisopropanolamine salt, triisopropanolamine salt and the like.

Among the ascorbic acids, ascorbic acid and ascorbate such as sodium ascorbate and potassium ascorbate have a high ability to inhibit tyrosinase activity in the early stage.

There is a problem, however, that the ability to inhibit tyrosinase activity decreases over time. Therefore, in the present invention, from the viewpoint of the ability to inhibit tyrosinase activity and its stability, ascorbyl glucoside, sodium ascorbyl-2-phosphate, potassium ascorbyl-2-phosphate, magnesium ascorbyl-2-phosphate, calcium ascorbyl-2-phosphate and the like are preferably used.

In the present invention, it is important to use the (A) component and the (B-2) component in combination. When a ratio of both components (R2) is defined as the following equation, R2 is usually in the range of 0.0001 to 1,000, preferably 0.001 to 300, more preferably 0.01 to 50.

$$R2=[\text{Concentration of } (A) \text{ component } (\mu g/mL)/\text{Concentration of } (B\text{-}2) \text{ component } (mg/mL)].$$

If the ratio of the (A) component is excessively low, the ability to inhibit tyrosinase activity cannot be enhanced. To the contrary, if the ratio is excessively high, the benefit of improving the ability to inhibit tyrosinase activity by using the (B-2) component together decreases, and economical disadvantage arises due to an increased amount of expensive (A) component According to the present invention, the ability to inhibit tyrosinase activity becomes excellent by using the (A) component and the (B-1) component or the (B-2) component in combination. Therefore, there can be provided an external preparation for skin for the purpose of whitening and beautifying skin, for example, skin care cosmetics such as milky lotion, cream, lotion, pack and cleanser: makeup cosmetics such as makeup base and liquid foundation: quasi-drugs such as ointment, dispersion, cream and external liquid.

<External Preparation for Skin>

The external preparation for skin of the present invention can be prepared according to a conventional method except that it contains the (A) component and the (B-1) or (B-2) component constituting the inhibitor of tyrosinase activity. The form of the external preparation for skin is not particularly limited, and examples thereof include skin care cosmetics such as milky lotion, cream, lotion, pack and cleanser, cosmetics such as lipstick and makeup cosmetics, quasi-drugs such as ointment, dispersion, cream, topical application and liquid medicine. There are no particular restrictions on the dosage form, and it can be in the form of solid, paste, mousse, gel, powder, solution, micro-emulsion, emulsion, powder dispersion, multilayer and the like.

A type of emulsion for preparing an emulsion-type external preparation for skin such as milky lotion or cream is not particularly limited, and examples thereof include O/W (oil-in-water type), W/O (water-in-oil type), W/O/W (water-in-oil-in-water type) and O/W/O (oil-in-water-in-oil type). Among these emulsions, a water-in-oil-in-water type emulsion containing the (A) component in the innermost water phase and the (B) component in the outermost water phase can be expected to have an improved stability of preparations as well as increased stability of the (A) component, thereby it is expected that the action to inhibit tyrosinase activity can be more effectively exerted.

A content of the (A) component (α-lipoic acid derivative) in the external preparation for skin of the present invention is preferably $1\times10^{-5}$ to 1% by mass, more preferably $5\times10^{-5}$ to 0.5% by mass based on a weight of dry solid. If the content of the (A) component is excessively small, a sufficient whitening effect due to suppression of tyrosinase activity cannot be obtained. Even if it is excessively increased, a higher whitening effect cannot be obtained.

On the other hand, a content of the (B-1) component (human manganese SOD) in the external preparation for skin is preferably 3 to 30,000 units/100 g, more preferably 30 to 15,000 units/100 g. If the content of the (B-1) component is excessively small, the skin-whitening effect becomes insufficient. Conversely, if it is excessively increased, the skin-whitening effect does not increase, hence economic disadvantage arises.

The content of the (B-2) component (ascorbic acid compounds) is preferably 0.001 to 5.0% by mass, more preferably 0.1 to 3.0% by mass. If the content of the (B-2) component is excessively small, a sufficient skin-whitening effect due to suppression of tyrosinase activity cannot be obtained. Conversely, even if it is excessively increased, the formulation tends to become unstable.

In addition to the above-mentioned components (A) and (B), the external preparation for skin of the present invention may appropriately contain ingredients usually used in preparations such as cosmetics and quasi-drugs as long as the effects of the present invention are not impaired. Examples of such ingredients include water (purified water, hot spring water, deep sea water etc.), oily material, surfactant, metal soap, gelling agent, powder, alcohol, water-soluble polymer, film forming agent, resin, ultraviolet-ray protective agent, clathrate compound, antimicrobial agent, fragrance, deodorant, salt, pH adjuster, refreshing agent, animal-derived extract, microorganism-derived extract, plant-derived extract, blood flow promoter, astringent, antiseborrheic agent, active oxygen scavenger, cell activator, humectant, keratolytic agent, enzymes, hormones, vitamins, etc. These ingredients may be added alone or in combination of two or more compounds.

The oily material is not limited as long as it is used in ordinary cosmetics. It may be a natural oil or a synthetic oil, and any oils such as hydrocarbons, waxes, fatty acids, higher alcohols, ester oils, silicone oils and fluorinated oils regardless of properties such as solid, semi-solid and liquid can be used. For example, there are exemplified hydrocarbons such as squalane, squalene, ceresin, paraffin, paraffin wax, liquid paraffin, pristane, polyisobutylene, microcrystalline wax and petrolatum; waxes such as beeswax, carnauba wax, candelilla wax, spermaceti; animal oils such as beef tallow, beef bull fat, beef bone fat, hardened beef tallow, hydrogenated oil, turtle oil, lard fat, horse fat, mink oil, liver oil and egg yolk oil; lanolin derivatives such as lanolin, liquid lanolin, reduced lanolin, lanolin alcohol, hard lanolin, acetylated lanolin, lanolin fatty acid isopropyl, POE lanolin alcohol ether, POE lanolin alcohol acetate, lanolin fatty acid polyethylene glycol and POE hydrogenated lanolin alcohol ether; fatty acids such as lauric acid, myristic acid, palmitic acid, stearic acid, behenic acid, undecylenic acid, oleic acid, arachidonic acid, docosahexaenoic acid (DHA), isostearic acid, 12-hydroxystearic acid;

higher alcohols such as lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecanol, cholesterol, phytosterol, sitosterol, lanosterol, POE cholesterol ether and monostearyl glycerin ether (batyl alcohol);

ester oils such as diisobutyl adipate, 2-hexyldecyl adipate, di-2-heptylundecyl adipate, n-alkyl glycol monoisostearate, isocetyl isostearate, trimethylolpropane triisostearate, glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, neopentyl glycol dicaprate, triethyl citrate, 2-ethylhexyl succinate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid ester, isopropyl myristate, octyldodecyl myristate, 2-hexyldecyl myristate, myristyl myristate, hexyldecyl dimethyl octanoate, ethyl laurate, hexyl laurate, N-lauroyl-L-glutamic acid-2-octyl dodecyl ester and diisostearyl malate;

glyceride oils such as acetoglyceride, glyceryl triisooctanoate, glyceryl triisostearate, glyceryl triisopalmitate, glyceryl tri-2-ethylhexanoate, glyceryl monostearate, glyceryl di-2-heptylundecanoate and glyceryl trimyristate; higher alkoxy-modified silicones such as dimethyl polysiloxane, methylphenyl polysiloxane, methyl hydrogen polysiloxane, octamethyl cyclotetrasiloxane, decamethyl cyclopentasiloxane, dodecamethyl cyclohexasiloxane, tetramethyl tetrahydrogen cyclotetrasiloxane and stearoxy silicone; silicone-based oils such as higher fatty acid-modified silicone, silicone resin, silicone rubber and silicone oil; and fluorinated oily materials such as perfluoropolyether, perfluorodecalin and perfluorooctane.

As the surfactant, anionic, cationic, nonionic and amphoteric active agents can be used. Examples of the anionic surfactant include fatty acid soaps such as sodium stearate and triethanolamine palmitate, alkyl ether carboxylic acids and salts thereof, carboxylates such as condensates of amino acids and fatty acids, alkylsulfonic acids, alkenesulfonates, sulfonates of a fatty acid ester, sulfonates of a fatty acid amide, alkyl sulfonates and formalin condensates thereof, salts of alkyl sulfuric acid ester, salts of secondary higher alcohol sulfate, salts of alkyl and allyl ether sulfate, salts of fatty acid ester sulfate, salts of fatty acid alkylolamide sulfate, salts of sulfuric acid ester such as Turkey red oil, alkyl phosphates, ether phosphates, alkyl allyl ether phosphates, amide phosphates, and N-acylamino acid based surfactant.

Examples of the cationic surfactant include amine salts such as alkylamine salt, polyamine and amino alcohol fatty acid derivative, alkyl quaternary ammonium salt, aromatic quaternary ammonium salt, pyridinium salt and imidazolium salt. Examples of the nonionic surfactant include sorbitan fatty acid ester, glycerin fatty acid ester, polyglycerin fatty acid ester, propylene glycol fatty acid ester, polyethylene glycol fatty acid ester, sucrose fatty acid ester, polyoxyethylene alkyl ether, polyoxypropylene alkyl ether, polyoxyethylene alkyl phenyl ether, polyoxyethylene fatty acid ester, polyoxyethylene sorbitan fatty acid ester, polyoxyethylene sorbitol fatty acid ester, polyoxyethylene glycerin fatty acid ester, polyoxyethylene propylene glycol fatty acid ester, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane, polyoxyalkylene-alkyl co-modified organopolysiloxane, alkanolamide, sugar ether and sugar amide. Examples of the amphoteric surfactant include betaine, aminocarboxylate, imidazoline derivatives and the like.

As the metallic soap, aluminum 12-hydroxystearate, zinc stearate, aluminum stearate, calcium stearate, magnesium stearate, zinc myristate, magnesium myristate, zinc cetyl phosphate, calcium cetyl phosphate, sodium zinc cetyl phosphate, zinc laurate, zinc undecylenate and the like can be mentioned.

Examples of the gelling agent include amino acid derivatives such as N-lauroyl-L-glutamic acid and α, γ-di-n-butylamine; dextrin fatty acid esters such as dextrin palmitate, dextrin stearate, dextrin 2-ethylhexanoate palmitate; sucrose fatty acid esters such as sucrose palmitate and sucrose stearate; sorbitol-benzylidene derivatives such as monobenzylidene sorbitol, dibenzylidene sorbitol; organic modified clay minerals such as dimethyl benzyl dodecyl ammonium montmorillonite clay and dimethyl dioctadecyl ammonium montmorillonite clay.

As the powder, any of inorganic powder, organic powder and pigment regardless of its form such as spherical, needle-like and plate-like, its particle size such as fumes, fine particles and pigment grade and its particle structure such as porous and non-porous can be mentioned. Examples of the inorganic powder include magnesium oxide, barium sulfate, calcium sulfate, magnesium sulfate, calcium carbonate, magnesium carbonate, talc, synthetic mica, mica, kaolin, sericite, muscovite, synthetic mica, phlogopite, biotite mica, lithia mica, silicic acid, anhydrous silicic acid, aluminum silicate, magnesium silicate, magnesium aluminum silicate, sulfur-containing aluminum silicate, calcium silicate, barium silicate, strontium silicate, metal tungstate, hydroxyapatite, vermiculite, higilite, montmorillonite, zeolite, ceramic powder, dibasic calcium phosphate, alumina, aluminum hydroxide, boron nitride and the like.

Examples of the organic powder include polyamide powder, polyester powder, polyethylene powder, polypropylene powder, polystyrene powder, polyurethane, benzoguanamine powder, polymethyl benzoguanamine powder, tetrafluoroethylene powder, polymethyl methacrylate powder, silk powder, nylon powder, 12 nylon, 6 nylon, styrene-acrylic acid copolymer, divinylbenzene-styrene copolymer, vinyl resin, urea resin, phenol resin, fluororesin, silicone resin, acrylic resin, melamine resin, epoxy resin, polycarbonate resin, microcrystalline fiber powder and lauroyl lysine.

Examples of the color pigment include inorganic red pigments such as iron oxide, iron hydroxide and iron titanate; inorganic brown pigments such as γ-iron oxide; inorganic yellow pigments such as yellow iron oxide and ocher; inorganic black pigments such as black iron oxide and carbon black; inorganic violet pigments such as manganese violet and cobalt violet; inorganic green pigments such as chromium hydroxide, chromium oxide, cobalt oxide and cobalt titanate; inorganic blue pigments such as prussian blue and ultramarine blue; pigments obtained by laking tar dyes; pigments obtained by laking natural dyes, and composite powders obtained by combining these powders. Examples of the pearl pigment include mica coated with titanium oxide, bismuth oxychloride, bismuth oxychloride coated with titanium oxide, talc coated with titanium oxide, fish scale foil and colored mica coated with titanium oxide. Examples of the metal powder pigment include aluminum powder, copper powder and stainless steel powder.

Examples of the tar dye includes Red No. 3, Red No. 104, Red No. 106, Red No. 201, Red No. 202, Red No. 204, Red No. 205, Red No. 220, Red No. 226, Red No. 227, Red No. 228, Red 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207. Examples of the natural dye include carminic acid, laccaic acid, carthamin, braziline and crocin. Powders such as the above-mentioned inorganic powders, organic powders, pigments and tar dyes may be complexed, or surface-treated with an oily material, a silicone, or a fluorine compound.

Examples of the ultraviolet protective agents include cinnamic acid type ultraviolet absorbers such as 2-ethylhexyl p-methoxycinnamate, isopropyl p-methoxycinnamate, diethanolamine p-methoxyhydrocinnamate, glyceryl mono-2-ethylhexanoate di-p-methoxycinnamate, octyl methoxycinnamate and methyl diisopropyl cinnamate; benzophenone type ultraviolet absorbers such as 2,2'-dihydroxy-4-methoxybenzophenone, 2-hydroxy-4-methoxybenzophenone-5-sulfuric acid, sodium 2-hydroxy-4-methoxybenzophenone-5-sulfate, 2,4-dihydroxybenzophenone, 2,2'-dihydroxy-4,4'-dimethoxybenzophenone, 2,2'-dihydroxy-4-methoxybenzophenone, 2,2',4,4'-tetrahydroxybenzophenone, 2-hydroxy-4-n-octoxybenzophenone; and benzoic acid type ultraviolet absorbers such as p-aminobenzoic acid, ethyl p-aminobenzoate, butyl p-aminobenzoate, 2-ethylhexyl p-dimethylaminobenzoate, glyceryl p-aminobenzoate and amyl p-aminobenzoate.

In addition, examples of the ultraviolet protective agents include salicylic acid type ultraviolet absorbers such as 2-ethylhexyl salicylate, triethanolamine salicylate, homomenthyl salicylate, dipropylene glycol salicylate, methyl salicylate, ethylene glycol salicylate, phenyl salicylate, amyl salicylate, benzyl salicylate, isopropyl benzyl salicylate and potassium salicylate; dibenzoylmethane type ultraviolet absorbers such as 4-t-butyl-4'-methoxydibenzoylmethane, 4-isopropyldibenzoylmethane, 4-methoxydibenzoylmethane and 4-t-butyl-4'-hydroxydibenzoylmethane; anthranilic acid type ultraviolet absorbers such as menthyl-o-aminobenzoate, 2-phenyl-benzimidazole-5-suluric acid, 2-phenyl-5-methylbenzoxazole, 3-(4-methylbenzylidene) camphor, 2-ethylhexyl-2-cyano-3,3'-diphenyl acrylate, 2-ethyl-2-cyano-3,3'-diphenyl acrylate, 2-(2'-hydroxy-5-methylphenyl) benzotriazole and menthyl anthranilate; urocanic acid type ultraviolet absorber such as ethyl urocanate; titanium oxide, zirconium oxide and cerium oxide.

Examples of the alcohols include lower alcohols such as ethanol and isopropanol; polyhydric alcohols such as glycerin, diglycerin, ethylene glycol, diethylene glycol, triethylene glycol, propylene glycol, dipropylene glycol, 1,3-butylene glycol and polyethylene glycol; and the like.

Examples of the water-soluble polymer include plant-derived polymers such as gum arabic, tragacanth, galactan, carob gum, guar gum, karaya gum, carrageenan, pectin, agar, algae colloid, trant gum, locust bean gum and galactomannan; microorganism-derived polymers such as xanthan gum, dextran, succinoglycan and pullulan; animal-derived polymers such as casein, albumin and gelatin; starch-derived polymers such as starch, carboxymethyl starch and methylhydroxypropyl starch; cellulose polymers such as methylcellulose, ethylcellulose, methylhydroxypropyl cellulose, carboxymethylcellulose, hydroxymethylcellulose, hydroxypropylcellulose, nitrocellulose, sodium cellulose sulfate, sodium carboxymethylcellulose, crystalline cellulose and powdered cellulose; alginic acid based polymers such as sodium alginate and propylene glycol alginate; vinyl polymers such as polyvinyl methyl ether, carboxy vinyl polymers, alkyl modified carboxy vinyl polymers; polyoxyethylene based polymers; polyoxyethylene-polyoxypropylene copolymer based polymers; acrylic polymers such as sodium polyacrylate, polyethyl acrylate, and polyacrylamide; polyethyleneimine; cationic polymer; and inorganic water-soluble polymers such as bentonite, laponite and hectorite. The water-soluble polymer also include a film forming agent such as polyvinyl alcohol and polyvinyl pyrrolidone.

Examples of the antibacterial agent include benzoic acid, sodium benzoate, phenol, sorbic acid, potassium sorbate, p-oxybenzoic acid ester, p-chloromethacresol, hexachlorophene, benzalkonium chloride, chlorhexidine chloride, trichlorocarbanilide, photosensitizer, bis (2-pyridylthio-1-oxide) zinc, phenoxyethanol and thianthol, isopropylmethylphenol and the like. Examples of the pH adjuster include potassium carbonate, sodium bicarbonate, ammonium bicarbonate and the like. Examples of the refreshing agent include L-menthol, camphor and the like.

Examples of the cell activators include nucleic acid-related substances such as deoxyribonucleic acids and salts thereof, adenylate derivatives such as adenosine triphosphate and adenosine monophosphate and salts thereof, ribonucleic acids and salts thereof, cyclic AMP, cyclic GMP, flavin adenine nucleotides, guanine, adenine, cytosine, thymine, xanthine and its derivatives such as caffeine and theophylline and salts thereof; extracts derived from animals such as mammals, birds, shellfish, insects, fish, molluscs, crustaceans such as bovine blood extract, serum deproteinized extract, spleen extract, egg component of birds, cockscomb extract, shell extract, shellfish extract, royal jelly, silk protein and its degradation products or derivatives thereof, hemoglobin or decomposition products, lactoferrin or degradation products thereof, molluscan extracts such as spodoptera and fish meat extractse; extracts derived from microorganisms selected from fermented metabolites such as yeast extract, lactic acid bacteria extract and bifidobacterium extract.

Examples of the cell activator include vitamin A group such as retinol and its derivatives such as retinol palmitate and retinol acetate, retinal and its derivatives, dehydroretinal and carotenoid (e.g. carotene); vitamin B group such as thiamines such as thiamine hydrochloride and thiamine sulfate, riboflavins such as riboflavin and riboflavin acetate, pyridoxines such as pyridoxine hydrochloride and pyridoxine dioctanoate, flavin adenine nucleotide, cyanocobalamin, folic acids, nicotinic acids such as nicotinic acid amide and benzyl nicotinate and cholines; plant-derived extracts such as apricot extract, Ginkgo biloba extract, panax ginseng extract, barley extract, orange extract, cucumber extract, kiwi extract, lentinus edodes extract, equisetum extract, swertia extract, zizyphi fructus extract, capsicum extract, garlic extract, carrot extract, poria cocos sclerotium extract, peach extract, lettuce extract, lemon extract, Ganoderma lucidum extract, rosemary extract, hinokitiol and cepharanthin; α- and γ-linolenic acid, eicosapentaenoic acid and their derivatives, estradiol and its derivatives and salts thereof, and organic acids such as glycolic acid, succinic acid, lactic acid and salicylic acid, their derivatives and salts thereof. The cell activator may be used solely or in combination of two of more.

Examples of the active oxygen removing agent include mannitol, bilirubin, cholesterol, tryptophan, histidine, quercetin, quercitrin, catechin, catechin derivatives, rutin, rutin derivatives, taurine, thiotaurine, eggshell membrane extract, gallic acid, gallic acid derivatives, yeast extract, Ganoderma lucidum extract, alnus firma sieb. et zucc. fruit extract, geranium extract, moutan bark extract, melissa extract, parsley extract and Lycii Cortex extract; vitamin A group such as retinol and its derivatives (e.g. retinol palmitate and retinol acetate), retinal and its derivatives and dehydroretinal; vitamin B group such as thiamines such as thiamine hydrochloride and thiamine sulfate, riboflavins such as riboflavin and riboflavin acetate, pyridoxines such as pyridoxine hydrochloride and pyridoxine dioctanoate, flavin adenine nucleotide, cyanocobalamin, folic acids, nicotinic acids such as nicotinic acid amide and benzyl nicotinate and cholines; vitamin D group such as ergocalciferol, cholecalciferol and dihydroxystanal; vitamin E group such as tocopherol and its derivatives (e.g. dl-α-, dl-β- or dl-γ-tocopherol, dl-α-tocopherol acetate, dl-α-tocopherol nicotinate, dl-α-tocopherol linoleate, dl-α-tocopherol succinate) and ubiquinones; dibutylhydroxytoluene and butylhydroxyanisole.

Examples of the humectant include alkali simple hot spring water, deep ocean water, mucopolysaccharides and salts thereof such as hyaluronic acid, chondroitin sulfate, dermatan sulfate, heparan sulfate, heparin and keratan sulfate, proteins such as collagen, elastin and keratin and or derivatives thereof including salts thereof, phospholipids derived from soybean and eggs, glycolipid, ceramide, mucin, honey, erythritol, maltose, maltitol, xylitol, xylose, pentaerythritol, fructose, dextrin and its derivatives, mannitol, sorbitol, inositol, succharides such as trehalose and glucose, urea, amino acids and derivatives thereof including salts thereof such as asparagine, aspartic acid, alanine, arginine, isoleucine, orthinin, glutamine, glycine, glutamic acid and its derivatives, cysteine, cystine, citrulline, threonine, serine, tyrosine, tryptophan, theanine, valine, histidine, hydroxylysine, hydroxyproline, pyrrolidone carboxylic acid and its salts, proline, phenylalanine, methionine and lysine Examples of other humectants include D-panthenol, avocado extract, almond oil, locust bean extract, rice extract, strawberry extract, fennel extract, malva sylvestris extract, coptis japonica extract, olive oil, lamium album extract, cocoa butter, oat extract, hedera extract, Sasa veitchii extract, gardenia extract, grapefruit extract, geranium extract, gentian extract, burdock extract, clematis vitalba extract, sesame extract, cactus extract, Saponaria officinalis extract, ginger extract, rehmannia glutinosa root extract, shea butter, spiraea ulmaria extract, cnidium officinale extract, malva sylvestris extract, Thymus vulgaris extract, camellia extract, corn extract, cordyceps sinensis extract, potentilla tormentilla extract, houttuynia cordata extract, ophiopogon japonicus extract, lupinus perennis extract, hamamelis virginiana extract, mentha extract, green mentha extract, western mentha extract, parsley extract, rose extract, sunflower extract, hinoki extract, luffa cylindrica extract, prune extract, butcher's bloom extract, borage oil, peony extract, jojoba oil, lime tree extract, hop extract, pine extract, silybum marianum extract, macadamia nut oil, cydonia oblonga extract, Lithospermum erythrorhizon extract, meadowfoam oil, Melissa extract, centaurea cyanus extract, lily extract, Yuzu extract, lime extract, lavender extract, gentiana scabra extract, sanguisorba officinalis extract and apple extract. These humectants may be used solely or in combination of two or more.

Examples of the vitamins include vitamin K group such as phytonadione, menaquinone, menadione and menadiol; vitamin P group such as eriocitrin and hesperidin; biotin, carnitine and ferulic acid.

Examples of the blood circulation promoters include nonylic acid vanillylamide, capsaicin, zingerone, cantharis tincture, ichthammol, α-borneol, inositol hexanicotinate, cyclandelate, cinnarizine, tolazoline, acetylcholine, verapamil, γ-oryzanol and the like.

There are mentioned tannic acid as a skin astringent agent, thiantrol as an anti-seborrheic agent, and lipase and papain as an enzyme.

Examples of the skin-whitening agent include ascorbic acid derivatives other than the (B-2) component and salts thereof, cysteine and its derivatives such as N, N'-diacetylcystine dimethyl, glabridin, glabrene, liquiritin, isoliquyritin, placenta extract, hydroquinone and its derivatives such as arbutin, resorcin and its derivatives, ferulic acid and caffeic acid, and their derivatives and glutathione. Specific examples of the ascorbic acid derivatives include L-ascorbic acid alkyl ester, L-ascorbic acid sulfuric acid ester and the like. Specific examples of the salt of ascorbic acid derivatives include alkali metal salts such as sodium salt, potassium salt and the like, alkaline earth metal salts such as calcium salts and magnesium salts, and the like.

More specifically, there can be mentioned ascorbic acid derivatives such as ascorbyl palmitate, L-ascorbyl dipalmitate, L-ascorbyl isopalmitate, L-ascorbyl diisopalmitate, L-ascorbyl tetraisopalmitate, L-ascorbyl stearate, L-ascorbyl distearate, L-ascorbyl isostearate, L-ascorbyl diisostearate, L-ascorbyl myristate, L-ascorbyl dimyristate, L-ascorbyl isomyristate, L-ascorbyl diisomyristate, L-ascorbyl oleate, L-ascorbyl dioleate, L-ascorbyl 2-ethylhexanoate, sodium L-ascorbic acid sulfate, potassium L-ascorbic acid sulfate, magnesium L-ascorbate sulfate, calcium L-ascorbic acid sulfate and aluminum L-ascorbic acid sulfate; and extracts such as cicada extract, placenta extract, licorice extract, chamomile extract, animal- or plant-derived extract containing carotenoids, asparagus extract, pea extract, eijitsu extract, scutellaria root extract, Ononis spinosa extract, seaweed extract, raspberry extract, sophora root extract, mucuna birdwoodiana extract, periploca sepium extract, coffee extract, rice bran extract, wheat germ extract, Asiasari radix extract, hawthorn extract, Cassia mimosoides extract, white lily extract, peony extract, Inula britannica extract, soybean extract, tea extract, molasses extract, tomato extract, white lotus extract, beech bud extract, grape extract, flor de manita extract, hop extract, rosa rugosa extract, pseudocydonia sinensis extract, saxifraga sarmentosa extract, eucalyptus extract, coix seed extract and momordica grosvenorii extract.

EXAMPLE

Hereinafter, the present invention will be further described with reference to specific examples. However, the present invention is not limited by these examples. The content of each ingredient is expressed in % by mass unless otherwise specified.

<Test for Evaluating Inhibition of Tyrosinase Activity>

A test solution having a volume of 2.0 mL was prepared by adding 0.1 mL of tyrosinase (derived from mushrooms, manufactured by Sigma, 100 units/mL) to a sample for evaluation, and then 0.1 M phosphate buffer solution having a pH of 6.5 was added. The test solution was incubated in a thermostat at 37° C. for 10 minutes, and then 1 mL of DOPA (3,4-dihydroxy-L-phenylalanine, 0.03% solution) was added. After 2 minutes of the addition, the test solution was subjected to measurement of absorbance at 475 nm.

Thus-obtained absorbance value was defined as D1. As a control, the same measurement was conducted on a test solution in which each sample was replaced with purified water, and the obtained absorbance value was defined as D2. An inhibition rate of tyrosinase activity was calculated by the following formula.

$$\text{Inhibition rate of tyrosinase activity (\%)} = (D2-D1)/D2 \times 100$$

Reference Example 1

Test for Evaluating Inhibition Ability of Tyrosinase Activity on Histidine Dithiooctanamide (Na/Zinc)

As an α-lipoylamino acid derivative for evaluation, histidine dithiooctanamide (Na/zinc) was used which is commercially available from Oga Research Co., Ltd. as "DM-His. Zn" and has a molecular weight of 430.84. Test solutions containing histidine dithiooctanamide (Na/zinc) in a content of 1.08 μg/mL (2.5 μM), 2.15 μg/mL (5 μM), 3.23 μg/mL (7.5 μM) or 4.31 μg/mL (10 μM) were prepared, and the inhibition rate of tyrosinase activity on each test solution was measured according to the above test method. The results are as follows.

| Concentration of histidine dithiooctanamide (Na/zinc) | Inhibition rate of tyrosinase activity (%) |
|---|---|
| 1.08 μg/mL | 13.2 |
| 2.15 μg/mL | 25.3 |
| 3.23 μg/mL | 53.6 |
| 4.31 μg/mL | 68.9 |

These results indicate that the inhibition rate of tyrosinase activity increases with increase of the content of histidine dithiooctanamide (Na/zinc). Based on the data, histidine dithiooctanamide (Na/zinc) was confirmed to be effective to inhibit tyrosinase activity. However, the ability to inhibit tyrosinase activity was not yet sufficient.

Reference Example 2

Test for Evaluating Inhibition Ability of Tyrosinase Activity on Human Manganese SOD As a human manganese SOD for evaluation, "yeast extract (SOD)" was used which is commercially available from Biox Technologies, and has a concentration of 3,000 units/mL. Test solutions containing human manganese SOD in a content of 3 units/mL, 15 units/mL or 150 units/mL were prepared, and the inhibition rate of tyrosinase activity on each test solution was measured according to the above test method. The results are as follows.

| Concentration of human manganese SOD | Inhibition rate of tyrosinase activity (%) |
|---|---|
| 3 units/mL | 4.53 |
| 15 units/mL | 3.74 |
| 150 units/mL | 4.66 |

These results indicate that the inhibitory effect of tyrosinase activity does not increase even when the concentration of human manganese SOD is increased, and sufficient properties to inhibit tyrosinase activity cannot be expected when human manganese SOD is used solely.

Reference Example 3

Test for Evaluating Inhibition Ability of Tyrosinase Activity on Ascorbyl Glucoside As an ascorbic acid derivative for evaluation, ascorbyl glucoside "AS-G" commercially available from Hayashibara Co., Ltd. was used. Test solutions containing ascorbyl glucoside in a content of 5 mg/mL, 10 mg/mL or 20 mg/mL were prepared, and the inhibition rate of tyrosinase activity on each test solution was measured according to the above test method. The results are as follows.

| Concentration of ascorbyl glucoside | Inhibition rate of tyrosinase activity (%) |
|---|---|
| 5 mg/mL | 8.4 |
| 10 mg/mL | 15.4 |
| 20 mg/mL | 26.8 |

These results indicate that, when ascorbyl glucoside is used solely, the inhibition rate of tyrosinase activity increases with increase of the concentration of ascorbyl glucoside, but the inhibitory effect of tyrosinase activity is insufficient as compared with histidine dithiooctanamide (Na/zinc).

Example 1

Test solutions were prepared according to Reference Example 1 and Reference Example 2 except that histidine dithioctanamide (Na/zinc) used in Reference Example 1 and human manganese SOD used in Reference Example 2 were used in combination so as to have proportions shown in Table 1, and the inhibition rate of tyrosinase activity was measured according to the above test method. Histidine dithioctanamide (Na/zinc) and human manganese SOD are respectively referred to as (A) component and (B-1) component in Table 1. Table 1 shows an inhibition rate of tyrosinase activity of each test solution as well as a degree of improvement as compared with a test solution containing histidine dithioctanamide (Na/zinc) solely. Table 1 also shows the results obtained in Reference Examples 1 and 2.

TABLE 1

| Composition | (B-1) component (unit/mL) | | | | | | | | | | | |
|---|---|---|---|---|---|---|---|---|---|---|---|---|
| | 0 | | | 3 | | | 15 | | | 150 | | |
| (A) component (μg/mL) | I | II | III | I | II | III | I | II | III | I | II | III |
| — | — | 0.0 | | — | 4.5 | | — | 3.7 | | — | 4.7 | |
| 1.08 | 0 | 13.2 | 1.00 | 2.78 | 22.0 | 1.67 | 13.89 | 20.6 | 1.56 | 138.90 | 16.0 | 1.21 |
| 2.15 | 0 | 25.3 | 1.00 | 1.40 | 43.3 | 1.71 | 6.98 | 65.7 | 2.60 | 69.80 | 61.1 | 2.42 |
| 3.23 | 0 | 53.6 | 1.00 | 0.93 | 72.7 | 1.36 | 4.64 | 90.7 | 1.69 | 46.40 | 78.1 | 1.46 |
| 4.31 | 0 | 68.9 | 1.00 | 0.70 | 93.3 | 1.35 | 3.48 | 95.9 | 1.39 | 34.80 | 97.3 | 1.41 |

I R1: Ratio of content of (B) component to content of (A) component

II Inhibition rate of tyrosinase activity (%)

III Inhibition rate of tyrosinase activity in the case of conbining human manganese SOD/Inhibition rate of tyrosinase activity in the case without addition of human manganese SOD As seen from these results, the ability to inhibit the tyrosinase activity of histidine dithioctanamide (Na/zinc) is remarkably improved by using histidine dithiooctanamide (Na/zinc) and human manganese SOD in combination.

Comparative Example 1

An ability to inhibit tyrosinase activity was measured in the same manner as Example 1 except that human manganese SOD was replaced by 0.5% by volume aqueous solution of copper/zinc SOD (1), "DISMUTIN BTJ", which is available from DSM Nutrition and has a concentration of 50,000 PIU/mL. The aqueous solution copper/zinc SOD (1) had a concentration of 250 PIU/mL. The concentration of histidine dithiooctanamide (Na/zinc) was 4.31 µg/mL. PIU indicates an enzyme unit measured by the pyrogallol autoxidation method.

As a result, the inhibition rate of tyrosinase activity was 38% that is between 16.1% in the case of using copper/zinc SOD (1) solely and 68.9% in the case of using histidine dithioctanamide (Na/zinc) solely. As seen from the data, copper/zinc SOD (1) has no function to improve the ability to inhibit tyrosinase activity of histidine dithiooctanamide (Na/zinc).

Comparative Example 2

An ability to inhibit tyrosinase activity was measured in the same manner as Comparative Example 1 except that copper/zinc SOD (1) was replaced by 0.5% volume aqueous solution of another copper/zinc SOD (2), "SOD yeast extract" that is available from Aria Co., Ltd. The inhibition rate of tyrosinase activity was 75.9% that is higher than 68.9% in the case of using histidine dithioctanamide (Na/zinc) solely, but does not reach 95.9% obtained in the present invention at all.

Comparative Example 3

Histidine dithiooctanamide (Na/zinc) was replaced by kojic acid, ascorbic acid derivative (ascorbyl glucoside) or arbutin which are known as a compound having the ability to inhibit tyrosinase activity, and an ability to inhibit tyrosinase activity in combination of each compound and histidine dithiooctanamide (Na/zinc) was evaluated according to Example 1. Human manganese SOD was added to become 150 units/mL. As to the other compounds, kojic acid, ascorbic acid derivative (ascorbyl glucoside) and arbutin were added to be 1.2% by mass, 2.0% by mass and 3.0% by mass, respectively.

The inhibition rate of tyrosinase activity in the case of using kojic acid solely was 45.6%, and one in the case of using kojic acid in combination with human manganese SOD was 47.4%. As seen from the comparison, there was hardly any effect due to the combination of both components. The inhibition rate of tyrosinase activity in the case of using ascorbic acid derivative solely was 21.9%, and one in the case of using ascorbic acid derivative in combination with human manganese SOD was 25.6%. As seen from the comparison, there was very limited improvement due to the combination of both components. The inhibition rate of tyrosinase activity in the case of using arbutin solely was 71.3%, and one in the case of using arbutin in combination with human manganese SOD was 69.7%. As seen from the comparison, there was no effect due to the combination of both components.

From the results of Example 1 and Comparative Examples 1 to 3 as described above, it can be understood that (1) the inhibition rate of tyrosinase activity is greatly improved only when using α-lipoyl amino acid derivative and human manganese SOD in combination thereof, and (2) the inhibition rate of tyrosinase activity cannot be improved when using, in place of α-lipoyl amino acid derivative, other compounds having the ability to inhibit tyrosinase activity in combination with human manganese SOD.

Example 2

<Preparation of Lotion>

A lotion was prepared according to the formulation and procedure indicated below.

Procedure:

To purified water, a moisturizer, an anti-fading agent, a buffer, histidine dithiooctanamide (Na/zinc) and human manganese SOD were added, and they were dissolved at room temperature to obtain a water phase. On the other hand, an alcoholic phase was obtained by adding an emollient agent, a surfactant, a preservative and a fragrance to ethanol at room temperature. The resultant alcoholic phase is added to the water phase.

Formulation (% by Mass):

| | | |
|---|---|---|
| Humectant: | 1,3-Butylene glycol | 6.0 |
| | Glycerol | 5.0 |
| | PEG 4000 | 3.0 |
| Emollient agent: | olive oil | 0.5 |
| Surfactant: | POE (20) sorbitan monostearate | 1.5 |
| | POE (5) oleyl alcohol ether | 0.3 |
| Ethanol: | | 10.0 |
| Perfume: | | Appropriate amount |
| Coloring agent: | | Appropriate amount |
| Preservative: | | Appropriate amount |
| Buffer: | | Appropriate amount |
| Anti-fading agent: | | Appropriate amount |
| Histidine dithiooctanamide (Na/zinc) *1 | | 0.5 |
| Human manganese SOD *2 | | 1.0 |
| Purified water: | | Balance |

*1: DM-His. Zn (available from Oga Research Co., Ltd.)
*2: Yeast extract (SOD) (available from Biox Technology Co., Ltd.)

Example 3

<Preparation of Oil-in-Water Emulsion Cream>

A cream was prepared according to the formulation and procedure indicated below.

Procedure:

A water phase was prepared by adding a moisturizer and an alkali to purified water and heating the mixture to 70° C. After heating and melting an oil component, a surfactant, a preservative and an antioxidant were added to the oil component and the mixture was adjusted to 70° C. to obtain an oil phase. The oil phase was added to the water phase, and resultant mixture was homogenized using a homomixer, and then cooled. Finally, histidine dithiooctanamide (Na/zinc), human manganese SOD and a fragrance dissolved in a small amount of purified water were added to the mixture, mixed and degassed.

Formulation (% by Mass):

| Oil component: | Stearic acid | 8.0 |
|---|---|---|
| | Stearyl alcohol | 4.0 |
| | Butyl stearate | 6.0 |
| Humectant: | Propylene glycol | 5.0 |
| Surfactant: | Glyceryl monostearate | 2.0 |
| Alkali: | Potassium hydroxide | 0.4 |
| Preservative: | | Appropriate amount |
| Antioxidant: | | Appropriate amount |
| Fragrance: | | Appropriate amount |
| Histidine dithiooctanamide (Na/zinc) *1 | | 0.1 |
| Human manganese SOD *2 | | 0.1 |
| Purified water: | | Balance |

Example 4

<Preparation of W/O/W (Water-in-Oil-in Water) Type Cream>

A cream was prepared according to the formulation and procedure indicated below.
Procedure:
(1) Step for Preparing an Intermediate Water-in-Oil Type Emulsion A water phase was prepared by adding a moisturizer, sodium chloride and histidine dithiooctanamide (Na/zinc) to purified water and mixing at 50° C. After heating and melting an oil component, a surfactant was added to the oil component and then the mixture was adjusted to 50° C. After addition of the water phase to the mixture, the resultant mixture was homogenized using Disper mixer, and then cooled to obtain an intermediate water-in-oil type emulsion.
(2) Step for Preparing a Water-in-Oil-in Water Type Cream Using the Intermediate Water-in-Oil Type Emulsion A water phase was prepared by adding a moisturizer to purified water and heating the mixture to 75° C. After heating and melting an oil component, the intermediate water-in-oil type emulsion prepared in Step (1), a surfactant, a preservative and an antioxidant were added to the oil component and the mixture is adjusted to 75° C. The mixture was added to the water phase, and the resultant mixture was homogenized using Disper mixer. Finally, human manganese SOD and a fragrance dissolved in a small amount of purified water were added to the mixture, mixed and degassed.
Formulation (% by Mass):

| (1) Intermediate water-in-oil emulsion | | |
|---|---|---|
| Oil component: | Squalane | 0.8 |
| | Ethylhexyl palmitate | 0.5 |
| Surfactant: | Hexaglyceryl polyricinoleate | 0.15 |
| | Diglyceryl monoisostearate | 0.05 |
| Humectant: | Glycerin | 5.0 |
| | Sorbitol | 0.05 |
| Purified water: | | 6.0 |
| Sodium chloride | | 0.2 |
| Histidine dithiooctanamide (Na/zinc) *1 | | 0.1 |
| (2) Water-in-oil-in water type cream | | |
| Oil component: | Squalane | 5.0 |
| | Ethylhexyl palmitate | 2.0 |
| | Microcrystalline wax | 2.0 |
| | Petrolatum | 2.0 |
| | Behenyl alcohol | 3.0 |
| Intermediate water-in-oil emulsion | | 12.85 |

| Surfactant: | Glyceryl monostearate | 2.0 |
|---|---|---|
| | Sodium stearoyl glutamate | 0.5 |
| Humectant: | 1,3-Butylene glycol | 5.0 |
| Preservative: | | Appropriate amount |
| Antioxidant: | | Appropriate amount |
| Fragrance: | | Appropriate amount |
| Human manganese SOD *2 | | 0.1 |
| Purified water: | | Balance |

Example 5

<Preparation of Cleansing Foam>

A cleansing foam was prepared according to the formulation and procedure indicated below.
Procedure:

An oil phase was prepared by heating and melting a mixture of a fatty acid, an emollient agent and a humectant at 70° C. After dissolving an alkali in purified water, the oil phase was added to the alkaline aqueous solution with stirring. The resultant mixture was sufficiently neutralized, and then a surfactant was added to the mixture. After conducting a mixing, the mixture was cooled. To the mixture, a chelating agent, a fragrance, histidine dithiooctanamide (Na/zinc) dissolved in a small amount of purified water and human manganese SOD were added, and then the resultant mixture was homogenized, cooled and defoamed.
Formulation (% by Mass):

| Oil component: | Stearic acid | 12.0 |
|---|---|---|
| | Mirystic acid | 14.0 |
| | Lauric acid | 5.0 |
| Emollient agent: | Jojoba oil | 3.0 |
| Alkali: | Potassium hydroxide | 5.0 |
| Humectant: | 70% Sorbitol aqueous solution | 15.0 |
| | Glycerin | 10.0 |
| | 1,3-Butylene glycol | 10.0 |
| Surfactant: | PEG (20) glyceryl monostearate | 2.0 |
| | Acyl methyl taurine | 4.0 |
| Chelating agent: | | Appropriate amount |
| Fragrance: | | Appropriate amount |
| Histidine dithiooctanamide (Na/zinc) *1: | | 0.5 |
| Human manganese SOD *2: | | 0.5 |
| Purified water: | | Balance |

Example 6

<Preparation of Liquid Foundation>

A liquid foundation was prepared according to the formulation and procedure indicated below.
Procedure:

The powder ingredients shown in the following formulation were thoroughly mixed and pulverized, and then added to the oil phase shown in the formulation. Next, the oil phase was homogenized using a homomixer, and then the water phase shown in the formulation was added to the oil phase, and the resultant mixture was treated with a homomixer. Subsequently, histidine dithiooctanamide (Na/zinc) dissolved in a small amount of purified water and human manganese SOD were added to the mixture, and the resultant mixture was homogenized and defoamed.

Formulation (% by Mass):

| Powder: | Hydrophobized talc | 7.0 |
| | Hydrophobized titanium dioxide | 12.0 |
| | Hydrophobized anhydrous silicic acid | 2.0 |
| | Nylon powder | 4.0 |
| | Hydrophobize color pigment | 2.0 |
| Oil phase: | Decamethylcyclopentasiloxane | 30.0 |
| | Rosin pentaerythritol ester | 1.5 |
| | Polyoxyethylene-modified dimethylpolysiloxane | 1.5 |
| Water phase: | Purified water: | just Balance |
| | 1,3-Butylene glycol | 4.0 |
| | Ethanol | 7.0 |
| Histidine dithiooctanamide (Na/zinc) *1: | | 0.1 |
| Human manganese SOD*2: | | 1.0 |

Example 7

<Preparation of Sunscreen Milky Lotion>

A sunscreen milky lotion was prepared according to the formulation and procedure indicated below.

Procedure:

Each of the oil phase and the water phase shown in the following formulation was heated to 70° C. After titanium dioxide was sufficiently dispersed in the oil phase, the water phase was added to the oil phase while performing a treatment using a homogenizer. After completion of homogenization, the mixture was cooled. Next, histidine dithiooctanamide (Na/zinc) dissolved in a small amount of purified water and human manganese SOD were added to the mixture, and the resultant mixture was homogenized and defoamed.

Formulation (% by Mass):

| Water phase: | Purified water: | Balance |
| | 1,3-Butylene glycol | 5.0 |
| Oil phase: | Octyl p-methoxycinnamate | 5.0 |
| | Oxybenzone | 3.0 |
| | 4-tert-butyl-4'-methoxydibenzoylmethane | 1.0 |
| | Hydrophobized titanium dioxide | 3.0 |
| | Squalane | 20.0 |
| | Decamethylcyclopentasiloxane | 20.0 |
| | Polyoxyethylene-modified dimethylpolysiloxane | 3.0 |
| | Organo-modified montmorillonite | 1.5 |
| | Preservative: | Appropriate amount |
| | Fragrance: | Appropriate amount |
| Histidine dithiooctanamide (Na/zinc) *1: | | 1.0 |
| Human manganese SOD *2: | | 1.0 |

Example 8

<Evaluation Test for Inhibition of Tyrosinase Activity in Combination of Histidine Dithiooctanamide (Na/Zinc) and Ascorbyl Glucoside>

Test solutions were prepared according to Reference Example 1 and Reference Example 3 except that histidine dithioctanamide (Na/zinc) used in Reference Example 1 and ascorbyl glucoside used in Reference Example 3 were used in combination so as to have proportions shown in Table 2, and the inhibition rate of tyrosinase activity was measured according to the above test method. Histidine dithioctanamide (Na/zinc) and ascorbyl glucoside are respectively referred to as (A) component and (B-2) component in Table 2. Table 2 shows an inhibition rate of tyrosinase activity of each test solution as well as a degree of improvement as compared with a test solution containing histidine dithioctanamide (Na/zinc) solely. Table 2 also shows the results obtained in Reference Examples 1 and 3.

TABLE 2

| | | | | | | | | | | | | |
|---|---|---|---|---|---|---|---|---|---|---|---|---|
| | | | | (B-2) component (mg/mL) | | | | | | | | |
| Coponent | | 0 | | | 5.0 | | | 10.0 | | | 20.0 | |
| (A) component (µg/mL) | I | II | III | I | II | III | I(R) | II | III | I(R) | II | III |
| — | — | 0 | | 0 | 8.4 | | 0 | 15.4 | | 0 | 26.8 | |
| 1.08 | — | 13.2 | 1.00 | 0.22 | 31.9 | 1.48 | 0.11 | 45.5 | 1.59 | 0.05 | 85.7 | 2.14 |
| 2.15 | — | 25.3 | 1.00 | 0.43 | 89.2 | 2.65 | 0.22 | 92.5 | 2.27 | 0.11 | 100.0 | 1.92 |

I R2: Ratio of content of (A) component to content of (B) component
II Inhibition rate of tyrosinase activity (%)
III Tyrosinase activity inhibition rate in the case of using both components/Sum of tyrosinase activity inhibition rate in the case of using each component alone As seen from these results, the combination of histidine dithiooctanamide (Na/zinc) and ascorbyl glucoside results in a remarkable improvement of the ability to inhibit tyrosinase activity as compared with the case of using each compound solely. For example, when using 2.15 µg/mL of histidine dithiooctanamide (Na/zinc) or 20.0 mg/mL of ascorbyl glucoside, the inhibition rate of tyrosinase activity was 25.3% or 26.8%, respectively, while, when using both compounds in combination, the inhibition rate of tyrosinase activity was 100%. This value corresponds to 1.92 times the sum of inhibition rates of tyrosinase activity (i.e. 52.1%) when each of both compounds is used solely.

Examples 9 to 11 and Comparative Examples 4 to 5

<Evaluation Test for Inhibition of Tyrosinase Activity in Combination of Histidine Dithiooctanamide (Na/Zinc) and Ascorbic Acid Derivatives>

An ability to inhibit tyrosinase activity was measured in the same manner as Example 8 except that ascorbyl glucoside used as (B-2) component was replaced by magnesium ascorbyl phosphate (5 mg/mL), sodium ascorbyl phosphate (5 mg/mL) or ascorbic acid (0.01 mg/mL). The concentration of histidine dithiooctanamide (Na/zinc) was 2.15 µg/mL. For comparison, compositions containing 3-O-ethylascorbic acid (2.5 mg/mL) or di-sodium ascorbyl sulfate (2.5 mg/mL) were also tested in the same manner. Table 3 shows an inhibition rate of tyrosinase activity of each test solution as well as a degree of improvement as compared with a case using each compound solely. Table 3 also shows the results obtained in Reference Examples 1.

TABLE 3

(A) component: 2.15 μg/mL

| | (B-2) component | I (R2) | II (%) (B) component only | II (%) Combination of (A) and (B) | III |
|---|---|---|---|---|---|
| Reference Example 1 | — | — | — | 25.3 | 1.00 |
| Example 9 | Magnesium ascorbyl phosphate | 0.43 | 11.1 | 89.1 | 2.45 |
| Example 10 | Sodium ascorbyl phosphate | 0.43 | 15.6 | 93.4 | 2.28 |
| Example 11 | Ascorbic acid | 215 | 28.7 | 100.0 | 1.85 |
| Comparative Exmple 4 | 3-O-ethylascorbic acid | 0.86 | 29.9 | 63.0 | 1.14 |
| Comparative Exmple 5 | Disodium ascorbyl sulfate | 0.86 | 40.5 | 40.8 | 0.62 |

R2: Ratio of amount of (A) component to amount of (B-2) component
Inhibition rate of tyrosinase activity (%)
Tyrosinase activity inhibition rate in the case of using both components/Sum of tyrosinase activity inhibition rate in the case of using each component alone As seen from these results, the ability to inhibit the tyrosinase activity of histidine dithioctanamide (Na/zinc) is remarkably improved by using histidine dithiooctanamide (Na/zinc) and ascorbic acid, magnesium ascorbyl phosphate or sodium ascorbyl phosphate in combination as compared with a case using each compound solely. On the other hand, when 3-O-ethylascorbic acid or disodium ascorbyl sulfate is used, sufficient ability to inhibit tyrosinase activity could not be obtained even when histidine dithiooctanamide (Na/zinc) is used in combination.

Comparative Example 6

An ability to inhibit tyrosinase activity was measured in the same manner as Example 8 except that ascorbyl glucoside was replaced by an aqueous solution of pyridoxine hydrochloride (vitamin B6) having a concentration of 5 mg/mL. The concentration of histidine dithiooctanamide (Na/zinc) was 2.15 μg/mL. Results are shown in Table 4.

TABLE 4

| | | Pyridoxine hydrochloride (mg/mL) | | | |
|---|---|---|---|---|---|
| Composition | | 0 | | 5.0 | |
| | (μg/mL) | II | III | II | III |
| (A) component | — | 0.0 | — | 42.9 | — |
| | 2.15 | 25.3 | 1.00 | 51.1 | 0.75 |

II Inhibition rate of tyrosinase activity (%)
III Tyrosinase activity inhibition rate in the case of using both components/Sum of tyrosinase activity inhibition rate in the case of using each component alone As seen from the results, even when histidine dithioctanamide (Na/zinc) and pyridoxine hydrochloride are used in combination, there is hardly improvement on the ability to inhibit tyrosinase activity as compared with the case using each compound solely.

Comparative Example 7

An ability to inhibit tyrosinase activity was measured in the same manner as Example 8 except that histidine dithiooctanamide (Na/zinc) was replaced by an aqueous solution of α-lipoic acid (available from Tateyama Kasei) having a concentration of 4.31 μg/mL. The concentration of ascorbyl glucoside was 5 mg/mL. Results are shown in Table 5.

TABLE 5

| | Ascorbyl glycoside (mg/mL) | | | | | |
|---|---|---|---|---|---|---|
| Composition | 0 | | | 5.0 | | |
| α-lipoic acid (μg/mL) | I | II (%) | III | I | II (%) | III |
| — | — | 0.0 | — | 0.0 | 8.4 | — |
| 4.31 | — | 0.7 | 1.00 | 0.86 | 9.8 | 1.07 |

I R2: Ratio of content of α-lipoic acid to content of (B-2) component
II Inhibition rate of tyrosinase activity (%)
III Tyrosinase activity inhibition rate in the case of using both components/Sum of tyrosinase activity inhibition rate in the case of using each component alone As seen from the results, in the case of α-lipoic acid, there is no sufficient improvement on the ability to inhibit tyrosinase activity even when ascorbyl glucoside is used in combination.

Example 12

<Preparation of Lotion>
A lotion was prepared according to the formulation and procedure indicated below.

Procedure:
To purified water, a moisturizer, an anti-fading agent, a buffer, histidine dithiooctanamide (Na/zinc), ascorbyl glucoside and a pH adjuster were added, and they were dissolved at room temperature to obtain a water phase. On the other hand, an alcoholic phase was obtained by adding an emollient agent, a surfactant, a preservative and a fragrance to ethanol at room temperature. The resultant alcoholic phase was added to the foregoing water phase.

Formulation (% by Mass):

| Humectant: | 1,3-Butylene glycol | 6.0 |
|---|---|---|
| | Glycerin | 5.0 |
| | PEG 4000 | 3.0 |
| Emollient agent: | olive oil | 0.5 |
| Surfactant: | POE (20) sorbitan monostearate | 1.5 |
| | POE (5) oleyl alcohol ether | 0.3 |
| Ethanol: | | 10.0 |
| Fragrance: | | Appropriate amount |
| Coloring agent: | | Appropriate amount |
| Preservative: | | Appropriate amount |

-continued

| Buffer: | Appropriate amount |
| --- | --- |
| Anti-fading agent: | Appropriate amount |
| Histidine dithiooctanamide (Na/zinc) *1 | 0.5 |
| Ascorbyl glucoside | 2.0 |
| pH adjuster: | Appropriate amount |
| Purified water: | Balance |

*1: DM-His. Zn (available from Oga Research Co., Ltd.)

Example 13

<Preparation of Oil-in-Water Cream>

An oil-in-water cream was prepared according to the formulation and procedure indicated below.
Procedure:

A water phase was prepared by adding moisturizer and alkali to purified water and heating to 70° C. while mixing the mixture. After heating and melting oil components, surfactant, preservative and antioxidant were added to the oil component and the mixture was adjusted to 70° C. to obtain an oil phase. The oil phase was added to the water phase, and resultant mixture was homogenized using a homomixer, and then cooled. Finally, histidine dithioocatnamide (Na/zinc), fragrance and ascorbyl glucoside dissolved in a small amount of purified water were added to the mixture, mixed and degassed.
Formulation (% by Mass):

| Oil component: | Stearic acid | 8.0 |
| --- | --- | --- |
| | Stearyl alcohol | 4.0 |
| | Butyl stearate | 6.0 |
| Humectant: | Propylene glycol | 5.0 |
| Surfactant: | Glyceryl monostearate | 2.0 |
| Alkali: | Potassium hydroxide | 0.4 |
| Preservative: | | Appropriate amount |
| Antioxidant: | | Appropriate amount |
| Fragrance: | | Appropriate amount |
| Histidine dithiooctanamide (Na/zinc) *1 | | 0.1 |
| ascorbyl glucoside | | 0.1 |
| pH adjuster: | | Appropriate amount |
| Purified water: | | Balance |

Example 14

<Preparation of W/O/W (Water-in-Oil-in-Water) Type Cream>

A cream was prepared according to the formulation and procedure indicated below.
Procedure:
(1) Step for Preparing an Intermediate Water-in-Oil Type Emulsion A water phase was prepared by adding a moisturizer, sodium chloride and histidine dithiooctanamide (Na/zinc) to purified water and mixing at 50° C. After heating and melting oil components, a surfactant was added to the oil component and the mixture was adjusted to 50° C. The water phase was added to the mixture, and the resultant mixture was homogenized using Disper mixer, and then cooled to obtain an intermediate water-in-oil type emulsion.

(2) Step for Preparing a Water-in-Oil-in Water Type Cream Using the Intermediate Water-in-Oil Type Emulsion A water phase was prepared by adding a moisturizer to purified water and heating to 75° C. while mixing the mixture. After heating and melting oil components, the intermediate water-in-oil type emulsion prepared in Step (1), a surfactant, a preservative and an antioxidant were added to the oil components and the mixture is adjusted to 75° C. The mixture was added to the water phase, and the resultant mixture was homogenized using Disper mixer and then cooled. Finally, ascorbyl glucoside and a pH adjuster dissolved in a small amount of purified water and a fragrance were added to the mixture, mixed and degassed.
Formulation (% by Mass):

| (1) Intermediate water-in-oil emulsion | | |
| --- | --- | --- |
| Oil component: | Squalane | 0.8 |
| | Ethylhexyl palmitate | 0.5 |
| Surfactant: | Hexaglyceryl polyricinoleate | 0.15 |
| | Diglyceryl monoisostearate | 0.05 |
| Humectant: | Glycerin | 5.0 |
| | Sorbitol | 0.05 |
| Purified water: | | 6.0 |
| Sodium chloride | | 0.2 |
| Histidine dithiooctanamide (Na/zinc) *1 | | 0.1 |
| (2) Water-in-oil-in water type cream | | |
| Oil component: | Squalane | 5.0 |
| | Ethylhexyl palmitate | 2.0 |
| | Microcrystalline wax | 2.0 |
| | Petrolatum | 2.0 |
| | Behenyl alcohol | 3.0 |
| Intermediate water-in-oil emulsion indicated as (1) above | | 12.85 |
| Surfactant: | Glyceryl monostearate | 2.0 |
| | Sodium stearoyl glutamate | 0.5 |
| Humectant: | 1,3-Butylene glycol | 10.0 |
| Preservative: | | Appropriate amount |
| Antioxidant: | | Appropriate amount |
| Fragrance: | | Appropriate amount |
| Ascorbyl glucoside | | 0.5 |
| Purified water: | | Balance |

Example 15

<Preparation of Cleansing Foam>

A cleansing foam was prepared according to the formulation and procedure indicated below.
Procedure:

An oil phase was prepared by heating and melting a mixture of a fatty acid, an emollient agent and a humectant at 70° C. After dissolving an alkali in purified water, the oil phase was added to the alkaline aqueous solution with stirring. The resultant mixture was sufficiently neutralized, and then a surfactant was added to the mixture. After conducting a mixing, the mixture was cooled and followed by addition of a chelating agent, a fragrance, Histidine dithiooctanamide (Na/zinc), a pH adjuster and ascorbyl glucoside dissolved in a small amount of purified water, and the resultant mixture was homogenized, cooled and defoamed.
Formulation (% by Mass):

| Oil component: | Stearic acid | 12.0 |
| --- | --- | --- |
| | Mirystic acid | 14.0 |
| | Lauric acid | 5.0 |

29
-continued

| Emollient agent: | Jojoba oil | 3.0 |
|---|---|---|
| Alkali: | Potassium hydroxide | 5.0 |
| Humectant: | 70% Sorbitol aqueous solution | 15.0 |
|  | Glycerin | 10.0 |
|  | 1,3-Butylene glycol | 10.0 |
| Surfactant: | PEG (20) glyceryl monostearate | 2.0 |
|  | Acyl methyl taurine | 4.0 |
| Chelating agent: |  | Appropriate amount |
| Fragrance: |  | Appropriate amount |
| Histidine dithiooctanamide (Na/zinc) *1: |  | 0.5 |
| Ascorbyl glucoside |  | 0.5 |
| pH adjuster |  | Appropriate amount |
| Purified water: |  | Balance |

Example 16

<Preparation of Liquid Foundation>

A liquid foundation was prepared according to the formulation and procedure indicated below.

Procedure:

The powder ingredients shown in the following formulation were thoroughly mixed and pulverized, and then added to the oil phase shown in the formulation. Next, the oil phase was homogenized using a homomixer, and then the water phase shown in the formulation was added to the oil phase, and the resultant mixture was treated with a homomixer. Subsequently, histidine dithiooctanamide (Na/zinc), a pH adjuster and sodium ascorbate dissolved in a small amount of purified water were added to the mixture, and then the resultant mixture was homogenized and defoamed.

Formulation (% by Mass):

| Powder: | Hydrophobized talc | 7.0 |
|---|---|---|
|  | Hydrophobized titanium dioxide | 12.0 |
|  | Hydrophobized anhydrous silicic acid | 2.0 |
|  | Nylon powder | 4.0 |
|  | Hydrophobized color pigment | 2.0 |
| Oil phase: | Decamethylcyclopentasiloxane | 30.0 |
|  | Rosin pentaerythritol ester | 1.5 |
|  | Polyoxyethylene-modified dimethylpolysiloxane | 1.5 |
| Water phase: | Purified water: | Balance |
|  | 1,3-Butylene glycol | 4.0 |
|  | Ethanol | 7.0 |
| Histidine dithiooctanamide (Na/zinc) *1: |  | 0.1 |
| Sodium ascorbate |  | 1.0 |
| pH adjuster |  | Appropriate amount |

Example 17

<Preparation of Sunscreen Milky Lotion>

A sunscreen milky lotion was prepared according to the formulation and procedure indicated below.

Procedure:

Each of the oil phase and the water phase shown in the following formulation was heated to 70° C. After titanium dioxide was sufficiently dispersed in the oil phase, the water phase was added to the oil phase while performing a treatment using a homogenizer. After completion of homogenization, the mixture was cooled. Next, histidine dithiooctanamide (Na/zinc), a pH adjuster and magnesium ascorbyl phosphate dissolved in a small amount of purified water were added to the mixture, and then the resultant mixture was homogenized and defoamed.

30
Formulation (% by Mass):

| Water phase: | Purified water: | Balance |
|---|---|---|
|  | 1,3-Butylene glycol | 5.0 |
| Oil phase: | Octyl p-methoxycinnamate | 5.0 |
|  | Oxybenzone | 3.0 |
|  | 4-tert-butyl-4'-methoxydibenzoylmethane | 1.0 |
|  | Hydrophobized titanium dioxide | 3.0 |
|  | Squalane | 20.0 |
|  | Decamethylcyclopentasiloxane | 20.0 |
|  | Polyoxyethylene-modified dimethylpolysiloxane | 3.0 |
|  | Organo-modified montmorillonite | 1.5 |
|  | Preservative: | Appropriate amount |
|  | Fragrance: | Appropriate amount |
| Histidine dithiooctanamide (Na/zinc) *1: |  | 1.0 |
| Magnesium ascorbyl phosphate: |  | 3.0 |
| pH adjuster |  | Appropriate amount |

INDUSTRIAL APPLICABILITY

The tyrosinase activity inhibitor of the present invention has a remarkably improved ability to inhibit tyrosinase activity as compared with the case where the α-lipoic acid derivative is used solely. Hence, it is useful as a material for preparing cosmetics, quasi-drugs and the like. The external preparation for skin containing the tyrosinase activity inhibitor can effectively inhibit tyrosinase activity, and is useful as a cosmetic product and quasi-drugs which are excellent in skin-whitening effect.

The invention claimed is:

1. A tyrosinase activity inhibitor comprising a combination of (A) histidine dithiooctanamide (Na/zinc)

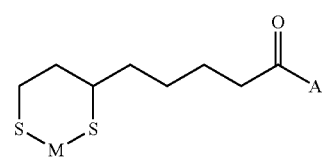

(1)

and (B-2) at least one of ascorbyl glucoside and salts thereof, wherein, when the tyrosinase activity inhibitor is a combination of said (A) component and said (B-2) component, the tyrosinase activity inhibitor has a ratio (R2) of the (A) component content to the (B-2) component content calculated based on the following formula being from 0.05 to 2.15

$R2 = [\text{Concentration of } (A) \text{ component } (\mu g/mL)/\text{Concentration of } (B\text{-}2) \text{ component } (mg/mL)]$.

2. An external preparation for skin comprising the tyrosinase activity inhibitor according to claim 1.

3. The external preparation for skin according to claim 2, wherein the external preparation for skin is a cosmetic.

4. The external preparation for skin according to claim 2, wherein a content of the (A) component is $1 \times 10^{-5}$ to 1% by mass, and a content of the (B-2) component is 0.01 to 3.0% by mass.

5. The external preparation for skin according to claim 2, wherein a dosage form is selected from solid, paste, mousse, gel, powder, solution, micro-emulsion, emulsion, powder dispersion and multilayer.

6. The external preparation for skin according to claim 5, wherein the dosage form is an emulsion.

7. The external preparation for skin according to claim 6, wherein the emulsion is O/W (oil-in-water type), W/O (water-in-oil type), W/O/W (water-in-oil-in-water type) or O/W/O (oil-in-water-in-oil type).

\* \* \* \* \*